(12) United States Patent
Martin et al.

(10) Patent No.: US 8,771,613 B2
(45) Date of Patent: Jul. 8, 2014

(54) LARGE VOLUME ANALYTE PRECONCENTRATOR

(75) Inventors: Michael Martin, Louisville, KY (US);
Robert Keynton, Louisville, KY (US);
Thomas Roussel, Louisville, KY (US);
Kevin M. Walsh, Louisville, KY (US);
Douglas J. Jackson, New Albany, IN (US); John Naber, Goshen, KY (US);
Julia W. Abersold, Floyds Knob, IN (US); Richard B. Hageman, III, Louisville, KY (US); Suraj Alexander, Anchorage, KY (US); Scott Cambron, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 13/056,091

(22) PCT Filed: Jul. 31, 2009

(86) PCT No.: PCT/US2009/052483
§ 371 (c)(1),
(2), (4) Date: May 23, 2011

(87) PCT Pub. No.: WO2010/014950
PCT Pub. Date: Feb. 4, 2010

(65) Prior Publication Data
US 2011/0214482 A1    Sep. 8, 2011

Related U.S. Application Data

(60) Provisional application No. 61/137,554, filed on Jul. 31, 2008.

(51) Int. Cl.
*G01N 30/00* (2006.01)
*G01N 30/08* (2006.01)

(52) U.S. Cl.
USPC .............. 422/527; 422/69; 422/88; 422/400; 73/23.41; 73/25.05

(58) Field of Classification Search
USPC ................ 422/527, 400, 69; 73/23.41, 25.05
See application file for complete search history.

(56) References Cited

U.S. PATENT DOCUMENTS 3,768,300 A   10/1973   Nemeth
4,011,301 A   3/1977    Young
(Continued)

FOREIGN PATENT DOCUMENTS

DE    19851821 A1    5/2000
EP    0649337 B1     9/1996
(Continued)

OTHER PUBLICATIONS

European Patent Office; European Search Report; Aug. 28, 2013; pp. 1-7; European Patent Office; the Netherlands.

(Continued)

*Primary Examiner* — Sally Merkling
(74) *Attorney, Agent, or Firm* — Wyatt, Tarrant & Combs, LLP; Stephen C. Hall

(57) ABSTRACT

A large volume preconcentrator device for concentrating analytes. A housing accepts an analyte vapor flow, and a plurality of collection surfaces are disposed within the housing. A selectively actuatable heater is disposed on each of the plurality of collection surfaces. At least one selectively actuatable damper is disposed within the housing for selectively restricting a collection flow.

14 Claims, 2 Drawing Sheets

(56) References Cited

U.S. PATENT DOCUMENTS

| | | |
|---|---|---|
| 4,698,071 A | 10/1987 | Elias |
| 4,805,441 A | 2/1989 | Sides et al. |
| 4,839,143 A | 6/1989 | Vora et al. |
| 4,935,040 A | 6/1990 | Goedert |
| 4,964,309 A | 10/1990 | Jenkins |
| 5,014,541 A | 5/1991 | Sides et al. |
| 5,035,776 A | 7/1991 | Knapp et al. |
| 5,053,343 A | 10/1991 | Vora et al. |
| 5,083,019 A | 1/1992 | Spangler |
| 5,092,155 A | 3/1992 | Rounbehler et al. |
| 5,092,218 A | 3/1992 | Fine et al. |
| 5,142,143 A | 8/1992 | Fite et al. |
| 5,174,797 A * | 12/1992 | Yow et al. ............... 95/20 |
| 5,395,589 A | 3/1995 | Nacson |
| 5,465,607 A | 11/1995 | Corrigan et al. |
| 5,578,271 A | 11/1996 | Simon et al. |
| 5,690,763 A | 11/1997 | Ashmead et al. |
| 5,707,502 A | 1/1998 | McCaffrey et al. |
| 5,720,798 A | 2/1998 | Nickerson et al. |
| 5,753,832 A | 5/1998 | Bromberg et al. |
| 5,792,423 A | 8/1998 | Markelov |
| 5,817,012 A | 10/1998 | Schoendorfer |
| 5,847,291 A | 12/1998 | Green et al. |
| 5,854,431 A | 12/1998 | Linker |
| 5,932,482 A | 8/1999 | Markelov |
| 5,970,803 A | 10/1999 | Staples et al. |
| 6,001,308 A | 12/1999 | Marlow et al. |
| 6,022,748 A | 2/2000 | Charych et al. |
| 6,057,162 A | 5/2000 | Rounbehler et al. |
| 6,066,295 A | 5/2000 | Bernstein et al. |
| 6,085,601 A | 7/2000 | Linker |
| 6,087,183 A | 7/2000 | Zaromb |
| 6,171,378 B1 | 1/2001 | Manginell et al. |
| 6,239,428 B1 | 5/2001 | Kunz |
| 6,242,195 B1 | 6/2001 | Idusogie et al. |
| 6,257,835 B1 | 7/2001 | Kaehler |
| 6,295,860 B1 | 10/2001 | Sakairi et al. |
| 6,316,268 B1 | 11/2001 | Yang |
| 6,326,615 B1 | 12/2001 | Syage et al. |
| 6,345,545 B1 | 2/2002 | Linker et al. |
| 6,354,160 B1 | 3/2002 | Staples et al. |
| 6,442,997 B1 | 9/2002 | Mergerle et al. |
| 6,485,987 B1 | 11/2002 | Charych et al. |
| 6,527,835 B1 | 3/2003 | Manginell et al. |
| 6,619,143 B2 | 9/2003 | Danylewych-May et al. |
| 6,666,907 B1 | 12/2003 | Manginell et al. |
| 6,706,091 B1 | 3/2004 | Robinson et al. |
| 6,759,013 B2 | 7/2004 | Kaltenbach et al. |
| 6,811,587 B1 | 11/2004 | Lorey |
| 6,869,501 B2 | 3/2005 | Davidson et al. |
| 6,893,879 B2 | 5/2005 | Peterson et al. |
| 6,914,220 B2 | 7/2005 | Tian et al. |
| RE38,797 E | 9/2005 | Linker |
| 6,989,891 B2 | 1/2006 | Braig et al. |
| 7,104,112 B2 | 9/2006 | Bonne |
| 7,118,712 B1 * | 10/2006 | Manginell et al. ............... 422/69 |
| 7,141,786 B2 | 11/2006 | McGann et al. |
| 7,244,288 B2 | 7/2007 | Belyakov |
| 7,273,517 B1 | 9/2007 | Lewis et al. |
| 7,306,649 B2 | 12/2007 | Boyle et al. |
| 2002/0055184 A1 | 5/2002 | Naylor et al. |
| 2003/0106799 A1 | 6/2003 | Covington et al. |
| 2004/0035226 A1 | 2/2004 | Allen et al. |
| 2004/0035227 A1 | 2/2004 | Allen et al. |
| 2004/0060346 A1 | 4/2004 | Bonne et al. |
| 2005/0014134 A1 | 1/2005 | West |
| 2005/0095722 A1 | 5/2005 | McGill et al. |
| 2005/0226778 A1 * | 10/2005 | Houser et al. ............... 422/99 |
| 2005/0253061 A1 | 11/2005 | Cameron et al. |
| 2006/0257287 A1 | 11/2006 | Call |
| 2007/0084347 A1 | 4/2007 | Boyle et al. |
| 2007/0176092 A1 | 8/2007 | Miller et al. |
| 2008/0148815 A1 * | 6/2008 | Lucas et al. ............... 73/23.41 |
| 2009/0028208 A1 | 1/2009 | Martin |
| 2009/0090197 A1 | 4/2009 | Finlay |
| 2009/0249958 A1 | 10/2009 | Cambron et al. |
| 2010/0236341 A1 | 9/2010 | Martin et al. |

FOREIGN PATENT DOCUMENTS

| | | |
|---|---|---|
| EP | 0502998 B1 | 7/1999 |
| GB | 2243917 A | 11/1991 |
| WO | 9735174 A1 | 9/1997 |
| WO | 0140793 A1 | 6/2001 |
| WO | 2004052540 A2 | 6/2004 |
| WO | 2004083806 A2 | 9/2004 |
| WO | 2005029030 A2 | 3/2005 |
| WO | 2006003646 A2 | 1/2006 |
| WO | 2006003646 A3 | 1/2006 |
| WO | 2006013396 A2 | 2/2006 |
| WO | 2006046077 A1 | 5/2006 |
| WO | 2006046988 A1 | 5/2006 |
| WO | 2006073434 A2 | 7/2006 |
| WO | 2006073440 A2 | 7/2006 |
| WO | 2006104603 A2 | 10/2006 |
| WO | 2007041551 A2 | 4/2007 |
| WO | 2007044473 A2 | 4/2007 |
| WO | 2007056488 A1 | 5/2007 |

OTHER PUBLICATIONS

Berger, T., et al.; "Development of Electrochemical Sensors for Trace Detection of Explosives and for the Detection of Chemical Warfare Agents"; Proceedings of the SPIE—The International Society for Optical Engineering; vol. 4038; pp. 452-461; 2000.

Cabalo, J., et al.; "Trace Detection of Explosives with Low Vapor Emissions by Laser Surface Photofragmentation-Fragment Detection Spectroscopy with an Improved Ionization Probe"; Applied Optics; vol. 44; No. 6; pp. 1084-1091; 20; Feb. 2005.

Da Silva, J.A.F., et al.; Simulations of silicon microstructure for preconcentration of metallic ions; Microelectronics Technology and Devices; SBMICRO 2003; Proceedings of the Eighteenth International Symposium; Sep. 2003; pp. 420-427; Pennington, NJ; USA.

Davidson, William R., et al.; "Vapor and Particle Sampling in the Detection of Terrorists Explosives"; Proc. 50th ASMS Conf. Mass Spectrom; Allied Top; pp. 697-698; 2002.

Ewing, R.G., et al.; "Detection of Volatile Vapours Emitted from Explosives with a Handheld Ion-Mobility Spectrometer"; Field Analytical Chemistry and Technology; vol. 5; No. 5; pp. 215-221; 2001.

Fisher, M, et al.; "Explosive Detection Using High-Volume Vapor Sampling and Analysis by Trained Canines and Ultra-Trace Detection Equipment"; Proceedings of the SPIE—The International Society for Optical Engineering; vol. 5403; No. 1; pp. 409-417; Apr. 12-16, 2004.

Goeringer, Douglas et al.; Comparison of Atmospheric Pressure Chemical Ionization and Atmospheric Sampling Glow Discharge Ionization Combined with Tandem Mass Spectrometry for Explosives Vapor Detection; Proc. 50th ASMS Conf. Mass Spectrom; Allied Top; pp. 707-708; 2002.

Hannum, David W., et al.; "Miniaturized Explosive Preconcentrator for Use in a Man-Portable Field Detection System"; International Nuclear Materials Management Conference; Phoenix, AZ; Aug. 2, 1999.

Ho, C.K., et al.; "Integrated Chemiresistor Sensors with Preconcentrators for Monitoring Volatile Organic Compounds in Water"; Proceedings of the 2005 World Water and Environmental Resources Congress; EWRI 2005: Impacts of Global Climate Change; Anchorage, Alaska; May 15, 2005.

Holland, R.M. et al.; "Handheld GC Instrumentation for Chemical Weapons Convention treaty verification inspections Monograph Title—Field screening methods for hazardous wastes and toxic chemicals, VIP-47"; vol. 1; Air and Waste Management Association; Pittsburgh, PA; 1995.

Hughes, David; "Explosive Detection Equipment Firms Develop Enhanced X-Ray and Vapor Technologies"; Aviation Week & Space Technology; vol. 134; No. 12; pp. 60-62; Mar. 25, 1991.

Hughes, R.C. et al.; "Chemical sensing with an integrated preconcentrator/chemiresistor array"; Chemical and Biological Sen-

(56) References Cited

OTHER PUBLICATIONS sors and Analytical Methods II Proceedings of the International Symposium; 2001; pp. 348-354; Electrochemical Society; Pennington, NJ; USA.
Hughes, R.C. et al.; "A MEMS Based Hybrid Preconcentrator/Chemiresistor Chemical Sensor"; Sep. 1, 2002.
Lucero, Daniel P.; "User Requirements and Performance Specifications for Explosive Vapor Detection Systems"; Journal of Testing & Evaluation; vol. 13; No. 3; pp. 222-233; 1985.
Martin, Michael, et al.; "Characterization of a Cascaded Micro-Preconcentrator Sampler for IMS"; International Symposium in Thun. Switzerland on Jul. 25-31, 2009.
Martin, Michael, et al.; "Microfabricated vapor preconcentrator for portable ion mobility spectroscopy"; Sensors and Actuators, B: Chemical; vol. 126; No. 2; Oct. 1, 2007.
McGill, R.A., et al.; "A micromachined preconcentrator for enhanced trace detection of illicit materials"; 2003 International Semiconductor Device Research Symposium; IEEE; Piscataway, NJ; USA.
McGill, R.A., et al.; "Choosing polymer coatings for chemical sensors"; American Chemical Society; Chemtech; Sep. 1994.
Owano, T.G., et al.; "Ultrasensitive Detection of Explosives Vapor Using Mid-IR Cavity Ring-Down Spectroscopy"; Technical Digest. Summaries of papers presented at the Conference on Lasers and Electro-Optics; Postconference Technical Digest; pp. 519-520; 2001.
Parmeter, J.E., et al.; "Development of a portable preconcentrator/ion mobility spectrometer system for the trace detection of narcotics"; Sandia National Labs; Report; Albuquerque, NM; Aug. 1997.
Parmeter, J.E., et al.; "Explosives detection portal for high-volume personnel screening"; Proceedings of the 1998 Enforcement and Security Technologies; Boston, MA 1999.
Parmeter, John, et al.; "Overview of Explosives Detection Research and Development in Department 5848 at Sandia National Laboratories"; 16th Annual NDIA Security Technology Symposium & Exhibition; Jun. 26-29, 2000.
Ritchie, Robert K., et al.; "Detection of Explosives, Narcotics, and Taggant Vapors by an Ion Mobility Spectrometry Particle Detector"; Proceedings of the SPIE—The International Society for Optical Engineering; vol. 2092; pp. 87-93; 1994.
Rodacy, Philip, J., et al.; "Unexploded ordnance classification sensor for underwater applications"; Sandia National Labs; Report; Albuquerque, NM Apr. 1, 2000.
Rhykerd, C., et al.; "Airport testing an explosives detection portal"; Institute of Nuclear Materials Management (INMM) annual meeting; Naples, FL; Jul. 26-30, 1998.
Sandia National Laboratories; "Micro Analytical Systems Department Technology—µChemLab, Fact Sheet"; Dec. 30, 2002.
Seman, G., et al.; "Detection of Hidden Explosives on Passenger Aircraft using Hand Searches, Bio-Sensors and Vapour Detectors"; Proceedings of the 1977 International Conference on Crime Countermeasures—Science and Engineering; pp. 65-84; 1977.
Sigman, M.E., et al.; "Performance Evaluation of an In-Injection Port Thermal Desorption/Gas-Chromatographic/Negative Ion Chemical Ionization Mass Spectrometric Method for Trace Explosive Vapour Analysis"; Analytical Chemistry; vol. 73; No. 4; pp. 792-798; Feb. 15, 2001.
Simoes, E.W., et al.; "Study of preconcentration of non-polar compounds in microchannels with constrictions"; Sensors and Actuators; vol. 115; No. 1; Lausanne, Switzerland; May 23, 2006; pp. 232-239.
Spicer, James B, et al.; "Overview: MURI Center on Spectroscopic and Time Domain Detection of Trace Explosives in Condensed and Vapor Phases"; Proc. SPIE Int Soc Opt Eng.; vol. 5089; No. 2; pp. 1088-1094; 2003.
Staples, Edward J., et al.; "Ultrahigh-Speed Chromatography and Virtual Chemical Sensors for Detecting Explosive and Chemical Warfare Agents"; IEEE Sensors J.; vol. 5; No. 4; pp. 622-631; Aug. 2005.

* cited by examiner

__US 8,771,613 B2__

LARGE VOLUME ANALYTE PRECONCENTRATOR

PRIORITY CLAIM AND REFERENCE TO RELATED APPLICATION

This application claims the benefit of U.S. Provisional Application Ser. No. 61/137,554, filed Jul. 31, 2008, under 35 U.S.C. Section 119, and also claims benefit as a National Stage Entry of PCT/US2009/52483, which has an international filing date of Jul. 31, 2009.

STATEMENT OF GOVERNMENT INTEREST

This application was made with Government assistance under Grant No. 2004-IJ-CX-K0555 issued by Department of Justice. The Government has certain rights in this invention.

TECHNICAL FIELD

A field of the invention is analyte collection. Embodiments of the invention may be useful, for example, in analyte detection and analysis systems and methods, as might be used for the collection, detection, and analysis of a wide range of vapors or gases, particulate, and/or liquid bound analytes.

BACKGROUND ART

Analyte detection is becoming increasingly important as a security and safety measure. Transportation, commercial, government, educational, and other facilities have a need for the sensitive and rapid detection of analytes, such as (but not limited to) those that are indicative of explosives or other substances that pose a threat. In addition, in industrial, residential, and commercial settings analyte detection can provide warning of particles or vapors that pose a health or safety risk. Example analytes that can be detected include hazardous materials such as but not limited to explosive-related materials, toxic industrial chemicals (TICS), or chemical or biological agents.

Analysis instruments have been developed and are under development to meet the need for detection of analytes. A non-limiting example analysis instrument currently being used in both portable and larger forms is the Ion Mobility Spectrometer (IMS). More particular examples of an IMS include the GE Vapor Tracer models, though other types of IMS may be used. Speed and sensitivity are primary concerns, and thus researchers and manufacturers seek to improve the speed and sensitivity of such analysis instruments.

A typical IMS device has separate particle and vapor modes. In a particle mode, an assembly is affixed to the device to accept and desorb particles from a substrate such as a swab (though other substrates are possible). The swab, for example, may be inserted into the assembly and heated to vaporize any collected particulates. The vapor is directed via vacuum into the instrument for analysis. Another assembly can be affixed to the device for vapor mode, a mode in which the device collects vapors for analyte detection.

Preconcentrators offer the opportunity to enhance the performance of any type of analysis instrument by increasing the concentration of analyte in a volume of fluid sent for analysis. Generally, preconcentrators collect analyte over a period of time (during adsorption) and then provide a concentrated fluid stream to the analysis instrument (during desorption).

Rapid preconcentration requires rapid heating. Accordingly, successful microscale preconcentrators have advantages regarding cycling and desorption, as heating to accomplish desorption can be conducted quickly and with low power. Example microscale preconcentrators are disclosed in U.S. Pat. No. 6,257,835 to Manginell et al., entitled "Chemical Preconcentrator with Integral Thermal Flow Sensor", and in U.S. Pat. No. 6,171,378 to Manginell et al., entitled "Chemical Preconcentrator". For example, a chemical preconcentrator may be formed from a substrate having a suspended membrane, such as low-stress silicon nitride. This work incorporates a flow over design.

Multiple stage designs are often used for high volume concentration. Examples of multiple stage designs are disclosed in U.S. Pat. No. 5,854,431 to Linker et al., entitled "Two Stage Preconcentrator for Vapor/Particle Detection", and U.S. Pat. No. 6,085,601 to Linker et al., entitled "Particle Preconcentrator".

Example microscale preconcentrators with a flow through design are disclosed in U.S. Published Patent Application No. 20050095722 (incorporated by reference herein), published May 5, 2005, and entitled "Micro scale Flow Through Sorbent Plate Collection Device", and in U.S. Published Patent Application No. 20050226778, published Oct. 13, 2005, and entitled "Micro scale Flow Through Sorbent Plate Collection Device". The flow through design has a number of advantages, one of which is increasing contact between analyte fluid flow and a sorbent in a collection area compared to typical flow over designs that would require creating a turbulent flow to match the level of analyte fluid-sorbent contact.

However, while one or more of the preconcentrators described above are suitable for low volume collection, high volume collection for continuous testing presents special challenges. One reason is that preconcentrators and analysis instruments have generally been designed to conduct sampling over small time periods. Accordingly, the volume of sample flow that can be accommodated is generally small.

DISCLOSURE OF THE INVENTION

According to embodiments of the present invention, a large volume preconcentrator device for concentrating analytes is provided. An example device comprises a housing that accepts an analyte vapor flow, and a plurality of collection surfaces are disposed within the housing. A selectively actuatable heater is disposed on each of the collection surfaces.

At least one selectively actuatable damper is disposed within the housing for selectively restricting a collection flow.

BEST MODE OF CARRYING OUT THE INVENTION

Figure 1A:
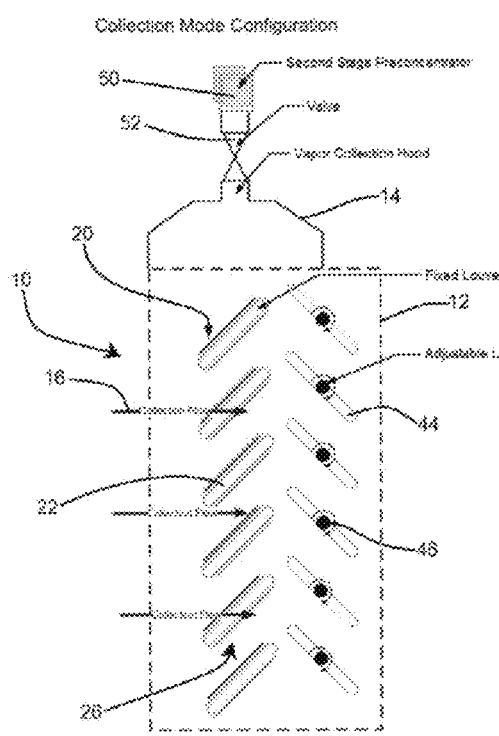
FIG. 1A shows a preconcentrator according to an embodiment of the present invention, configured for a collection mode.

Embodiments of the present invention provide, among other things, a preconcentrator suitable for collecting and desorbing a large volume of analyte. An example large volume preconcentrator is especially well-suited for vapor and particulate sampling within an HVAC system, though preconcentrators according to embodiments of the present invention may be used with other systems and/or analysis instruments. Such large volume preconcentrators may be used in concert with other preconcentrators to provide a multiple stage preconcentrator.

Generally, a large volume preconcentrator according to example embodiments of the invention includes a housing that accepts an analyte vapor flow, and houses one or more collection surfaces. Preferably, the collection surfaces are provided by surfaces of angled supports, for example louvers, disposed within the housing. Heaters may be provided on, for example affixed to, the collection surfaces. In a preferred embodiment, the heaters are affixed to both opposing surfaces (faces); that is, the collection surface and an opposed surface of each louver. Preferably, the heaters are thin and thermally isolated from the supporting louvers. In an example large volume preconcentrator, the heaters are adhered to both sides of the louvers. Alternatively, the heaters may be suspended in air to provide thermal insulation. The heaters on the collection face (the surface of the louver facing the collection flow of the analyte) are preferably (but not necessarily) coated with a sorbent material that collects target analytes while at a predetermined temperature, for example (but not necessarily) room temperature or ambient temperature, and desorbs upon heating to elevated temperatures (e.g., temperatures above the temperature used for collection). By thermally isolating the heaters from the supporting louvers, the amount of material to heat can be minimized, thus ensuring rapid heating and a concentrated analyte pulse.

In example embodiments, the narrow louvers may be fixed with respect to the housing (or at least can be fixed during collection and desorption), and the collection faces generally form a collection plane for collecting analyte. Immediately upstream of the collection plane, one or more selectively movable dampers are provided within the housing to selectively block fluid flow further upstream. In an example embodiment, adjustable louvers disposed within the housing are used alone or in combination as a valve to stop collection during desorption of the collected analyte. Once the heaters on the collection surfaces are heated, the pressure drop over the louver valve can then be used to drive analyte from the large volume preconcentrator to an outside system or device. Nonlimiting examples of outside systems or devices include a detector, an HVAC system, or an additional (e.g., second) preconcentator stage.

Preferred embodiments will now be discussed with respect to the drawings. The drawings include schematic figures that are not to scale, which will be fully understood by skilled artisans with reference to the accompanying description. Features may be exaggerated for purposes of illustration. From the preferred embodiments, artisans will recognize additional features and broader aspects of the invention.

Figure 1B:
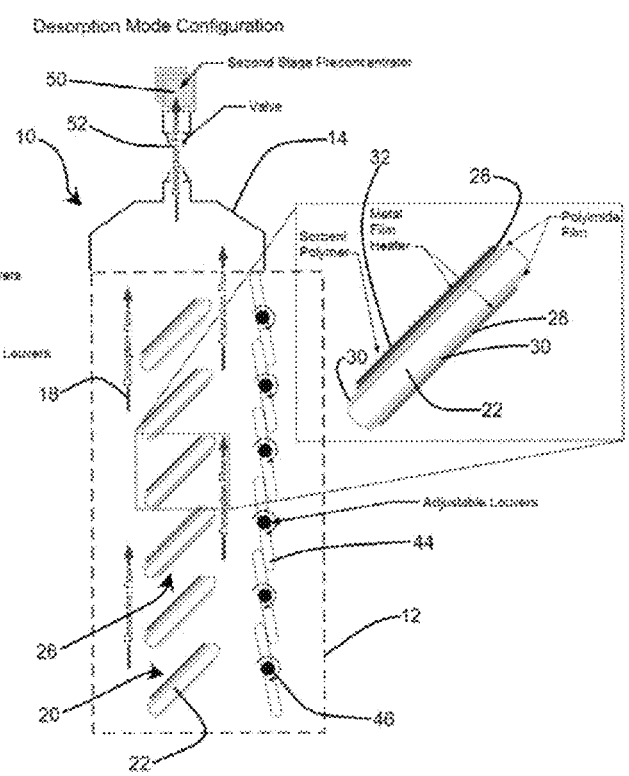
FIG. 1B shows the preconcentrator of FIG. 1, configured for a desorption mode.

FIGS. 1A-1B illustrate an example embodiment high volume preconcentrator 10. The preconcentrator 10 includes an outer housing 12, which may be of any of various materials and shapes. In the example shown in FIGS. 1A-1B, the outer housing 12 is shaped and positioned to be fitted to a vapor collection hood 14. The outer housing 12 is configured to accept fluid flow, such as an analyte vapor flow. For example, suitable openings may be provided in or on the housing 12 to allow fluid flow for collection 16 and desorption 18, as will be appreciated by those of ordinary skill in the art. The housing 12 preferably is thermally isolated so that nothing sticks to the housing (as a nonlimiting example, made of a metal that is easy to heat, such as aluminum). The shape of the housing 12 may be such that it aids in the particular flow desired (e.g., creating turbulent flow during collection so that more of the sample airflow will interact with sorbent, and laminar flow to help normal convection flow during desorption to exit the housing 12 and flow to an outside device). It will be appreciated, however, that this shape can vary significantly given design considerations that will be apparent to those of ordinary skill in the art. A front of the housing 12 may, but need not, include a screen to allow fluid flow while keeping or restricting contaminants from fouling preconcentrators.

To collect and desorb analyte, at least one and preferably a plurality of collection surfaces 20 are provided within the housing 12. In the example preconcentrator 10 shown in FIGS. 1A-1B, the collection surfaces 20 are provided by respective surfaces of a plurality of supports, for example louvers 22, that are disposed within the housing 12. Preferably, these supports, e.g., louvers 22, are thin and narrow. By thin, it is contemplated that the thickness (depth) of the louvers 22 be sufficiently small to reduce blocking of fluid flow during collection. If the louvers 22 are too thick, they may cause a pressure drop and take more power to heat up (both slower to heat as well as more power necessary to heat them). Optimal thickness (thinness) can vary depending on factors such as the velocity of the air. Nonlimiting example louvers have a thickness on the order of millimeters, though other thicknesses are contemplated. Narrowness of the louvers 22 refers to how wide the louvers are with respect to the airflow and the complete width of the housing 12. For example, a small number (as a nonlimiting example, two) of the louvers 22 may be provided that are wider, or alternatively there may be many narrow louvers (or numbers or louvers or widths in between), though each particular configuration may provide a (desired) larger surface area or meet other criteria (as a nonlimiting example, mechanical considerations as needed or desired).

The louvers 22 may be supported within the housing 12 in any suitable manner, and may be supported either independently or as one or more combined surfaces (e.g., in a frame). As shown in FIGS. 1A-1B, the louvers 22 may be aligned, such as in a vertical arrangement, but this is not necessary in all embodiments. For example, one or more of the collection surfaces 20 (e.g., surface of the louvers 22) may instead be offset from other collection surfaces so that they do not interfere with one another during a desorption phase.

The louvers 22 are preferably (but not necessarily) fixed in position with respect to the housing 12 (and thus are referred to as fixed louvers in some example embodiments), and may be angled so that the collection surfaces 20 face toward the collection flow 16 to collect the analyte, as shown in FIG. 1A. Accordingly, the collection surfaces 20 are also referred to as collection faces herein. It is preferred that the angle of attack and the velocity of the incoming fluid (e.g., air) maximize capture of vapor and particles, but this is not necessary in all embodiments. Preferably, the louvers 22 are also angled so that the collection surfaces 20 face away from the desorption flow 18 so that the desorption flow leads away from the collection surfaces. In other words, in a particular example embodiment, the louvers 22 may be angled such that a direction normal to the collection surfaces 20 is at least partly toward the collection flow 16 and at least partly in the direction of the desorption flow 18. A nonlimiting example for the angle of the louvers 22 is 45°. Surfaces of the louvers 22 provide both the collection surface 20 and an opposing surface 26.

For desorbing the analyte, as best shown in FIG. 1B, a heater 28 (preconcentrator element) is disposed over the collection surfaces 20, and preferably also over the opposing surfaces 26. An example heater 28 is a metal film heater. The heater 28 is preferably thin in comparison to the thickness of the louvers 22. Generally, the heater 28 is adequately thin so that the elements have a fast thermal time constant, for example less than a second. The heater 28 is preferably thermally isolated from the collection surfaces 20 and the opposing surfaces 26 via a thermal insulating layer 30. Alternatively, the heater 28 may be suspended in air to provide thermal insulation (the surface of the heater 28 provides the collection surface). It is also contemplated in other particular embodiments for the heaters 28 to be free-standing or suspended, in which case a surface of the heater would provide the collection surface. In this latter case, the supports can be reduced or eliminated.

In the example embodiment shown in FIG. 1B, the thermal insulating layer 30 is a polyimide film, and more particularly a 100 µm Kapton film. By thermally isolating the heater 28 from the collection surface 20 (and preferably also from the opposing surface 26) the amount of material to heat is minimized, providing more rapid heating as well as a concentrated analyte pulse.

For collecting analyte, the collection surfaces 20 preferably include a layer 32 of a sorbent material, as best shown in FIG. 1B. The layer of sorbent material can vary according to the analyte to be collected, as will be appreciated by those of ordinary skill in the art. A nonlimiting example sorbent material is a sorbent polymer.

Figures 2, 3:
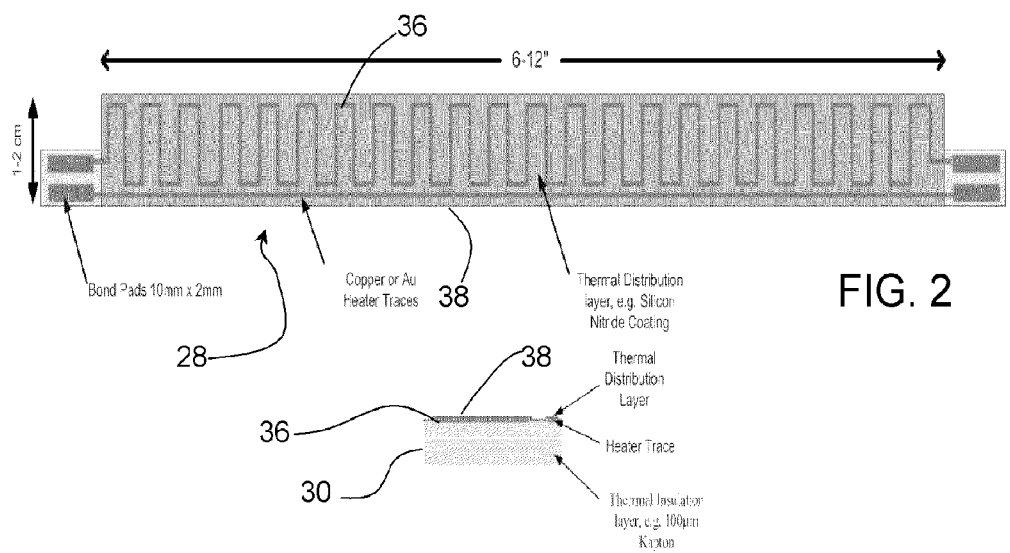
FIG. 2 shows an example strip heater for a collection surface, according to an embodiment of the present invention.
FIG. 3 is a sectional view showing layers of the example strip heater of FIG. 2.

A significant design consideration for vapor or particle preconcentrators based on thermal desorption is the rate at which the collection surface 20 can be heated. Preferred embodiment devices are designed to provide a thermal power density sufficient to heat only the top surfaces of the heater up to 230° C. or some appropriate thermal desorption temperature. A preferred embodiment strip heater 28 is shown in FIG. 2. Using flex circuit fabrication techniques, example heater traces 36 are sandwiched between a thermal distribution layer (high thermal conductivity) 38 and a thermal isolation layer (low thermal conductivity), such as layer 30. In the example heater 28 shown in FIGS. 2 and 3, the thermal distribution layer 38 is silicon nitride, the heater traces 36 are copper or gold, and the thermal isolation layer 30 is polyimide (e.g., Kapton). In a nonlimiting example, the strip heater 28 is 6-12" in length and 1-2 cm in width, though these can of course vary.

Not shown in FIGS. 2 and 3 (but shown in FIG. 1B) is the layer of sorbent material 32. A nonlimiting example sorbent material is the Naval Research Laboratory's HC polymer that selectively absorbs target analytes at room temperature and releases them at elevated temperatures approaching 200° C. This polymer layer may be deposited from its solvated form onto the thermal distribution layer 38 by inkjet printing, dip coating, or spray coating. Other sorbent materials may be used in the alternative. Thus, an example heater 28 may generally be composed of a stack comprising (from bottom to top); the thermal insulation layer 30 such as a polyimide, the heater trace 36, a thin dielectric layer (in some example embodiments) (not shown), which may be a relatively poor thermal conductor, the metallic thermal distribution layer 38, and the sorbent layer 32 (shown in FIG. 1B).

The individual heater strips 28 may be linked together in parallel over relatively large areas in order to simplify electrical connections and control electronics, or connected separately should they need, for example, to be individually addressed to allow for programmed sequential desorption. Those of ordinary skill in the art will appreciate electrical connections and control electronics that may be used. In the nonlimiting example heater 28 shown in FIGS. 2 and 3, bond pads 40 may be provided for electrically coupling a suitable electrical control system, such as control electronics (not shown), to the traces 36 for selectively actuating the heater. Further, the strip heaters 28 may be perforated with holes ranging from 10-1000 µm used to reduce pressure drop and improve collection efficiency for particles. In particular example embodiments, heater traces 36 may have their widths adjusted (and therefore thermal power density) as a function of position along the strip 28 in order to compensate for the temperature variations naturally accruing in a Joule heated bar. In other example embodiments, the heater trace 36 may take the form of a bar (as opposed to traces) with small perforations whose density or size varies along the bar length in order to compensate for the temperature variations naturally occurring in a Joule heated bar. The Joule heated conductor may have high thermal conductivity fingers used to carry thermal energy to the edges of the collector.

Referring again to FIGS. 1A and 1B, to stop collection during desorption and to control desorption flow, at least one, and preferably a plurality of, selectively movable dampers are provided within the housing 12 downstream of the collection plane (that is, downstream of where the collection flow 16 reaches the collection surfaces 20). In an example embodiment, the dampers are provided by a plurality of adjustable louvers 44 disposed immediately downstream (or disposed closely downstream). The example adjustable louvers 44 are positioned within the housing 12 and configured so that they can selectively rotate about a center 46 between at least a first position, shown in FIG. 1A, to provide respective gaps therebetween and thus allow fluid flow, and a second position, shown in FIG. 1B, to overlap one another, providing a barrier to fluid flow or otherwise restricting fluid flow. In this way, the example louvers 44 can be used as a valve to selectively allow collection during a collection mode (FIG. 1A) or selectively stop collection during a desorption mode (FIG. 1B). For selectively rotating the adjustable louvers 44, each of the adjustable louvers may be disposed about and supported by the center 46, which may be selectively pivotable. Alternatively or additionally, the louvers 44 themselves may be selectively movable to rotate the louvers about the center 46. Suitable devices or mechanisms for selectively rotating the louvers 44 will be understood by those of ordinary skill in the art.

Thus, in an example operation, during collection mode as shown in FIG. 1A, the heater 28 is either off or is sufficiently in a reduced state to allow collection for the collection surfaces 20. The collection surfaces 20 are positioned to face the direction of collection flow 16, and the louvers 44 are selectively positioned to allow fluid flow through the housing 12 for collection, so that analyte is collected on the sorbent layer 32 on the collection surfaces. Any suitable device for inducing flow may be used if desired to aid fluid flow through the housing 10.

After a suitable time period for collection (which can vary, as will be appreciated by those of ordinary skill in the art), the preconcentrator 10 then enters desorption mode (FIG. 1B). The heater 28 is activated on one or more of the collection surfaces 20 (and preferably on the opposed surfaces 26 as well) to desorb the analyte. As described above, the collection surfaces 20 are preferably positioned to face along the direction of desorption flow 18. The adjustable louvers 44 are rotated to substantially close fluid flow along the direction of the collection flow 16. During desorption flow 18, which may if desired be also induced by any suitable device, the desorbed analyte flows from the housing 12 to an outside device for collection.

As a nonlimiting example of an outside device, the preconcentrator 10 in FIGS. 1A-1B is shown leading into a second stage preconcentrator 50. This second stage preconcentrator 50 may be, for example, a flow-through preconcentrator such as that disclosed in U.S. Published Patent Application 20050095722 (incorporated by reference herein), published May 5, 2005, and entitled "Micro scale Flow Through Sorbent Plate Collection Device", and in U.S. Published Patent Application 20050226778, published Oct. 13, 2005, and entitled "Micro scale Flow Through Sorbent Plate Collection Device".

In an example embodiment, a selectively operable valve 52 may be provided in an outside device or between the housing 10 and the outside device to control fluid flow. For example, during collection mode (FIG. 1A), the valve 52 may be closed to prevent fluid flow to the outside device. During desorption mode (FIG. 1B), the valve 52 may be opened as shown to allow fluid (and analyte) flow to the outside device.

Large volume preconcentrators according to embodiments of the present invention, such as the preconcentrator 10, provide various features and advantages. For example, the example heater 28 and variations thereof offer more flexibility in terms of controlling the temperature profile over the collection surfaces in comparison to those based on metal or carbon meshes. Also, by utilizing dampers such as the louvers 44 as valves, the device 10 is more easily extended to arbitrarily large cross sectional areas as opposed to other macroscale preconcentrators that utilize expensive (and large) iris or gate valves. If the collection surfaces 20, and the heaters 28, are quite thin, the pressure drop will be lower than in designs that use metal or carbon mesh. The preferred embodiment housing 10 and variations thereof can be easily retrofitted over any of various outside devices. A nonlimiting example is a return air duct inlet.

It will be appreciated that the preconcentrator 10 shown in FIGS. 1A-1B and the heater 28 shown in FIGS. 2 and 3 are merely examples, and that variations are possible without departing from the spirit and scope of the present invention. For example, dampers, such as but not limited to louver valves, may be placed both upstream and downstream of the collection surfaces 20 in order to more carefully control desorption flow. The preconcentrator heaters 28 may be placed on adjustable (e.g., actuatable and/or pivotable) louvers for better control of the desorption flow profile. As another example, two independent louver valves and preconcentrators may be used side by side so that, while one half of the device is desorbing, the other half may continue to collect analyte. This configuration also minimizes disruption to the flow balance of an outside system, such as an HVAC system. The preconcentator heaters 28, preferably composed of thin micromachined polymer strips, may be suspended on a frame instead of supported by a set of louvers. In addition to the heaters 28, active coolers (e.g., Peltier coolers) may be added to one or more of the collection surfaces 20 to aid in the collection mode.

In another example embodiment, the louvers 44 or other supports may include one or more narrow slots running therethrough, defining generally rectangular spaces between the narrow slots. These narrow slots can allow tuning of the size of the particles that are captured on the collection surface based on the linear velocity, while allowing fibers and other contaminants to pass through.

Among many other possible variations, the preconcentrator 10 may be used in conjunction with an ionic or ozone based particle precipitation technology to enhance particle collection efficiency and/or analyte desorption from the source. The preconcentrator 10 may alternatively or additionally be used in conjunction with a laser desorption technique for release of analyte from targets.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

The invention claimed is:

1. A large volume preconcentrator device for concentrating analytes, the device comprising:
   a housing that accepts an analyte vapor collection flow;
   a plurality of fixed supports disposed within said housing, each of said plurality of supports respectively defining a collection surface, and the plurality of supports collectively defining a collection plane where the collection flow reaches the collection surfaces;
   a selectively actuatable heater disposed on the collection surface of each of said plurality of supports;
   a sorbent coating disposed on the collection surface of each of said plurality of supports; and
   a plurality of selectively actuatable dampers disposed within said housing and being rotatable about a pivot for selectively restricting a collection flow,
   wherein the plurality of selectively actuatable dampers are provided within the housing downstream of the collection plane, for selectively allowing and restricting collection flow.

2. The preconcentrator device of claim 1, wherein the collection surface of each of said plurality of supports is disposed to face toward a direction of a collection flow through said housing;
   wherein the collection surface of each of said plurality of supports is disposed to face along a direction of a desorption flow through said housing.

3. The preconcentrator device of claim 1, wherein each of said plurality of supports comprises louvers supported within said housing.

4. The preconcentrator device of claim 1, wherein said pivot is positioned at the center of said at least one selectively actuatable damper.

5. The preconcentrator device of claim 3, wherein each of the louvers are fixed.

6. The preconcentrator device of claim 3, wherein, for each of the louvers, said selectively actuatable heater is thermally isolated from the louver.

7. The preconcentrator device of claim 3, wherein each of the louvers comprise a plurality of narrow slots extending through the louvers and defining spaces between the narrow slots along the collection surface.

8. The preconcentrator device of claim 1, wherein each of said plurality of selectively actuatable dampers comprises adjustable louvers that are rotatable between a first position providing gaps between said dampers for allowing collection flow and a second position wherein said dampers overlap for restricting collection flow.

9. The preconcentrator device of claim 1, wherein each of said heaters comprises:
   a thermal insulation layer disposed over the collection surface;
   a heater trace disposed over said thermal insulation layer; and
   a thermal distribution layer disposed over said heater trace.

10. The preconcentrator device of claim 9, wherein each of said heaters further comprises:

a thin dielectric layer disposed between said heater trace and said thermal distribution layer.

11. The preconcentrator device of claim 1, wherein said housing is configured to interface with at least one of a return air duct, a vapor collection hood, and a second stage preconcentrator.

12. The preconcentrator device of claim 1, wherein, for each of said plurality of supports, said selectively actuatable heater is disposed on both the collection surface and an opposing surface of the support.

13. A large volume preconcentrator device for concentrating analytes, the device comprising:
   a housing for accepting an analyte vapor collection flow;
   means for supporting a plurality of fixed collection surfaces facing a direction of a collection flow, the collection surfaces collectively defining a collection plane where the collection flow reaches the collection surfaces;
   means for collecting analyte on the plurality of collection surfaces during the collection flow;
   means for selectively restricting the collection flow at a position downstream of the plurality of collection surfaces by actuation of a plurality of selectively actuatable dampers, each of which is rotatable about a pivot; and
   means for inducing a desorption flow from the collection surfaces.

14. A large volume preconcentrator device for concentrating analytes, the device comprising:
   a housing that accepts an analyte vapor collection flow;
   a plurality of collection surfaces fixably disposed within said housing, collectively defining a collection plane where the collection flow reaches the collection surfaces;
   a selectively actuatable heater disposed on each of the collection surfaces; and
   a plurality of selectively actuatable dampers disposed within said housing and downstream of said plurality of collection surfaces,
   wherein said selectively actuatable dampers are rotatable about a pivot and configured to occupy a first position providing gaps between said dampers for selectively allowing collection flow and a second position wherein said dampers overlap for selectively restricting a collection flow.

* * * * *